United States Patent
Arai et al.

(10) Patent No.: US 8,225,672 B2
(45) Date of Patent: Jul. 24, 2012

(54) METHOD FOR ASSESSING REMAINING LIFESPAN OF BOLT USED AT HIGH TEMPERATURES

(75) Inventors: Masahiko Arai, Hitachinaka (JP); Shinichi Kobayasji, Tokai (JP); Hiroyuki Doi, Tokai (JP); Hiroaki Chiba, Hitachi (JP); Takashi Haneishi, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 262 days.

(21) Appl. No.: 12/708,017

(22) Filed: Feb. 18, 2010

(65) Prior Publication Data
US 2010/0236333 A1    Sep. 23, 2010

(30) Foreign Application Priority Data
Mar. 19, 2009  (JP) ................. 2009-068790

(51) Int. Cl.
*G01N 3/00* (2006.01)
(52) U.S. Cl. .......................... 73/788; 73/808
(58) Field of Classification Search .......... 73/799, 73/808, 788
See application file for complete search history.

(56) References Cited

U.S. PATENT DOCUMENTS

| | | | |
|---|---|---|---|
| 3,957,542 A * | 5/1976 | Cina et al. ............ | 148/579 |
| 5,042,295 A * | 8/1991 | Seeley ............... | 73/112.03 |
| 6,568,254 B2 * | 5/2003 | Pross ............... | 73/112.01 |
| 6,810,748 B1 * | 11/2004 | Nishida et al. ......... | 73/788 |
| 6,935,552 B2 * | 8/2005 | Komai et al. .......... | 228/103 |
| 7,552,647 B2 * | 6/2009 | Soechting et al. ....... | 73/802 |
| 7,810,385 B1 * | 10/2010 | Narcus ............... | 73/112.01 |

FOREIGN PATENT DOCUMENTS

| | | |
|---|---|---|
| DE | 137 145 A1 | 8/1979 |
| JP | 58-092952 | 6/1983 |
| JP | 02-028554 | 1/1990 |
| JP | 2003-270220 | 9/2003 |
| JP | 2008-122345 A | 5/2008 |

OTHER PUBLICATIONS

Australian Office Action 2010200506 dated Mar. 9, 2011.

* cited by examiner

*Primary Examiner* — Max Noori
(74) *Attorney, Agent, or Firm* — Antonelli, Terry, Stout & Kraus, LLP.

(57) ABSTRACT

The present invention is intended to provide a method for assessing remaining lifespan of a bolt with higher precision than conventional methods, which can be applied to a bolt comprising a high alloy with fewer tissue changes caused by creep damage.

The present invention provides a method for assessing the remaining lifespan of a bolt used at high temperatures, including:

carrying out a creep test for a bolt material that constitutes a bolt to be assessed and determining a life-time and a life-elongation rate;

determining a time-temperature parameter based on the life-time and the creep test temperature;

creating a lifespan-assessment diagram by plotting the time-temperature parameter with respect to the life-elongation rate;

measuring a elongation rate between before and after the use of the bolt to be assessed; and assessing the remaining lifespan of the bolt with the use of the elongation rate between before and after the use of the bolt to be assessed and the lifespan-assessment diagram.

5 Claims, 5 Drawing Sheets

Before use    After use

Fig. 5

METHOD FOR ASSESSING REMAINING LIFESPAN OF BOLT USED AT HIGH TEMPERATURES

BACKGROUND OF THE INVENTION

The present invention relates to a method for assessing the remaining lifespan of a bolt used at high temperatures. In particular, the present invention relates to a method for assessing the remaining lifespan of a bolt appropriate for assessing the remaining lifespan of a bolt used at high temperatures by detecting deteriorated conditions in a non-destructive manner. Examples of such bolt include a bolt for a turbine pipe, a turbine valve and a turbine casing.

In general, rotor shafts, casings, casing bolts, and the like that constitute turbines are produced with the use of CrMoV-based low alloy steels, 12Cr steel ferritic stainless steels, and the like. In general, when such types of high-temperature members are subjected to stress loading for many hours in a high temperature atmosphere ranging from approximately 300° C. to 600° C., a carbide precipitates at a crystal grain boundary or in a crystal grain or void formation takes place at a grain boundary, resulting in deterioration of the members. Such deterioration might cause generation of cracks on a member constituting a turbine, eventually leading to a destructive turbine accident. In order to prevent such accident or to operate a turbine in an economical manner, it is important to correctly asses the lifespan of turbine parts.

In a conventional method for examining damaged conditions of a high-temperature member exposed to a high temperature atmosphere for many hours, a test piece is directly excised from a member that has been used in practice and the test piece is subjected to a destructive test. However, in recent years, an assessment method involving non-destructive testing has been used. In such case, damaged conditions can be evaluated while allowing a member to remain in an installed state.

For instance, JP Patent Publication (Kokai) No. 2-28554 A (1990) discloses a damage detection method for a high-temperature apparatus, comprising determining the shapes of microscopical defects that are generated in the tissue of a heat-resistant alloy used at high temperatures and comparing the results with predetermined quantitative damage based on the correlation between the microscopical defects and the quantitative damage so as to detect actual damage. However, for instance, in the cases of high Cr ferritic heat-resistant steels, which have been often used for high-temperature members in recent years, there are few tissue changes caused by creep damage and thus void formation is unlikely to take place at a grain boundary. Therefore, it is very difficult to assess remaining lifespan by observing microscopical defects.

JP Patent Publication (Kokai) No. 2003-270220 A (2003) discloses a lifespan prediction method, comprising irradiating a high-temperature member to be assessed with ultrasonic waves, determining the sonic velocity value thereof, and comparing the obtained sonic velocity value with that derived from an unused material and with that derived from a member subjected to load-free heat treatment, thereby calculating the remaining lifespan of the member. JP Patent Publication (Kokai) No. 58-92952 A (1983) discloses a method for predicting the lifespan of a high-temperature member based on the relationship between creep strain and decrease in hardness of a metallic material portion used at high temperatures. However, the above lifespan prediction methods are not satisfactory in terms of prediction precision.

SUMMARY OF THE INVENTION

It is an object of the present invention to provide a method for assessing the remaining lifespan of a high-temperature member with higher precision than conventional methods, which can be applied to a high-temperature member composed of a high alloy in which only few tissue changes are caused by creep damage.

The present inventors focused on the fact that, unlike a welded portion or the like, a bolt that is used at high temperatures becomes uniformly deformed because stress is uniformly applied thereto. They have found a novel assessment method for assessing the remaining lifespan of a bolt used at high temperatures. The present invention is described in summary as follows.

(1) A method for assessing the remaining lifespan of a bolt used at high temperatures, comprising:

carrying out a creep test for a bolt material that constitutes a bolt to be assessed and determining a life-time and a life-elongation rate;

determining a time-temperature parameter based on the life-time and the creep test temperature;

creating a lifespan-assessment diagram by plotting the time-temperature parameter with respect to the life-elongation rate;

measuring a elongation rate between before and after the use of the bolt to be assessed; and assessing the remaining lifespan of the bolt with the use of the elongation rate between before and after the use of the bolt to be assessed and the lifespan-assessment diagram.

(2) The method for assessing remaining lifespan of a bolt according to (1), wherein the life-time corresponds to the time to onset of the tertiary creep and the life-elongation rate corresponds to the elongation rate at the time to onset of the tertiary creep.

(3) The method for assessing remaining lifespan of a bolt according to (1) or (2), wherein the bolt used at high temperatures is for a turbine pipe, a turbine valve, or a turbine casing.

(4) The method for assessing remaining lifespan of a bolt according to any one of (1) to (3), wherein the bolt material is a ferritic forged steel containing 8% to 13% by mass of Cr.

(5) The method for assessing remaining lifespan of a bolt according to any one of (1) to (4), wherein the time-temperature parameter is Manson-Haferd parameter.

According to the assessment method of the present invention, the remaining lifespan of a bolt composed of a high alloy, such as a bolt used for a turbine, can be assessed via simple measurement technique with high precision. The method of the present invention contributes to safe operation of plants.

This specification incorporates the content of the specification of Japanese Patent Application No. 2009-068790, for which priority is claimed to the present application.

DESCRIPTION OF THE PREFERRED EMBODIMENTS

According to the method for assessing the remaining lifespan of the present invention, bolts used at high temperatures can be assessed. The term "high temperature" used herein refers to a temperature at which creep can be observed in a metallic material (generally at 0.4 $T_m$ ($T_m$: metal melting point)). The assessment method of the present invention is appropriate for assessing the remaining lifespan of bolts used at high temperatures of, for example, 300° C. or more, especially 500° C. or more, and particularly 600° C. or more. The term "bolt" used herein includes bolts of various shapes such as hexagonal bolts, stud bolts, and thru bolts. Bolts assessed in the present invention include bolts exposed to stress at high temperatures for many hours, which are used for, for example, fastening of pipes and casings for a variety of chemical plants and turbines. In particular, the present invention is appropriate for assessing the remaining lifespan of turbine bolts exposed to stress at high temperatures for many hours, such as bolts used for turbine pipes, turbine valves, turbine casings, and other turbine parts. Among turbine bolts, bolts used for turbines that are operated at 500° C. or more and particularly 600° C. or more especially tend to deteriorate due to exposure to high temperatures. In addition, there is a high probability that serious accidents could occur when such bolts are damaged. The assessment method of the present invention is appropriate for assessing the remaining lifespan of such turbine bolts with high precision. In addition, the term "turbine" used herein includes steam turbines, gas turbines, and other turbines operated at high temperatures.

Bolts show the feature that creep deformation takes place in a shank portion with a smaller diameter than that of a screw portion under exposure to stress at high temperatures for many hours, and that a substantially uniform cross-sectional area of a deformed part is observed. In addition, it can be regarded that the temperature is substantially uniform throughout the entire portion of a bolt. Therefore, the length of bolt elongation resulting from creep damage can be evaluated with high precision. Accordingly, the term "bolt" used in the present invention can also refer to a fastening member in which cross-sectional area of a deformed part due to creep deformation is substantially uniform.

The method for assessing the remaining lifespan of a bolt of the present invention comprises: a step of carrying out a creep test of a bolt material that constitutes a bolt to be assessed so as to obtain a life-time and a life-elongation rate; a step of obtaining a time-temperature parameter based on the life-time and the creep test temperature (the temperature at which the creep test is carried out); a step of creating a lifespan-assessment diagram by plotting the time-temperature parameter with respect to the life-elongation rate; a step of measuring a elongation rate between before and after the use of the bolt to be assessed; and a step of assessing the remaining lifespan of the bolt with the use of the elongation rate between before and after the use of the bolt to be assessed and the lifespan-assessment diagram.

Figure 1:
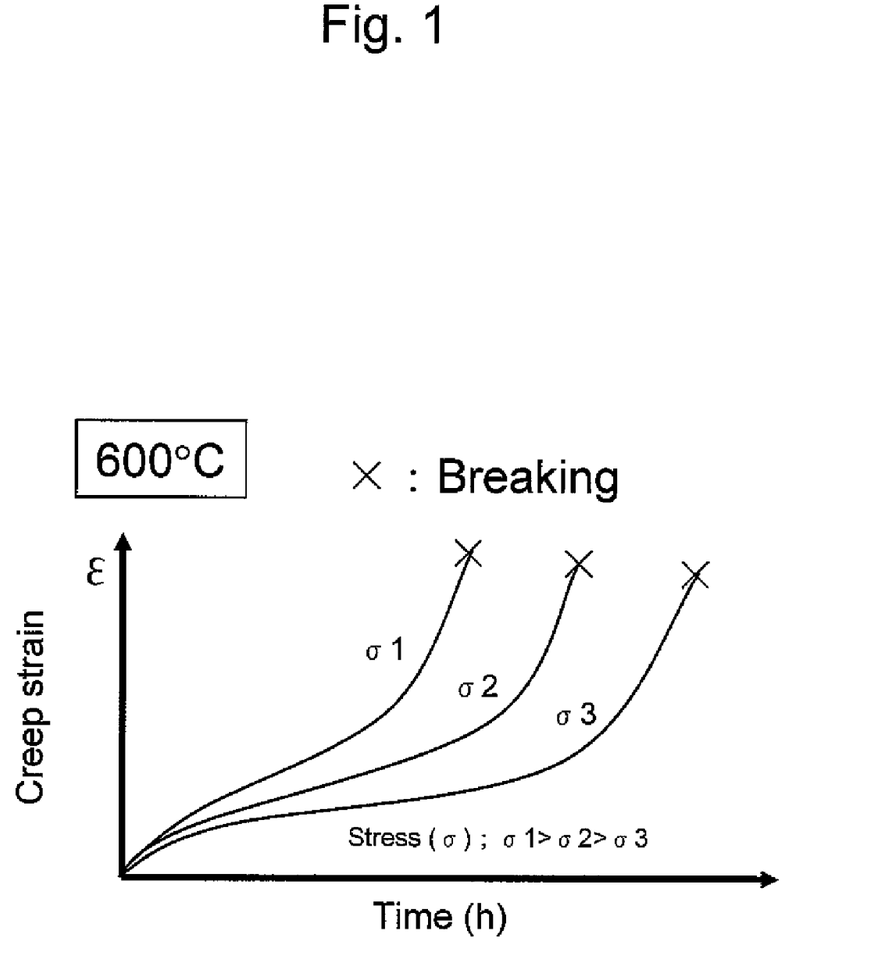
FIG. 1 schematically shows an example of a creep elongation curve.

A creep test for bolt materials can be carried out according to a method generally known to persons skilled in the art, such as the method defined as JIS Z 2271 (Japanese Industrial Standards Z 2271, creep and creep breaking test method for metallic materials) with the use of a round bar test piece with flange having a parallel portion diameter of 6 or 10 mm. The creep test is repeated a plurality of times by changing stress and/or test temperature. FIG. 1 schematically shows an example of a creep elongation curve obtained by a creep test conducted by applying three different stresses at a test temperature of 600° C. In addition, the breaking elongation, which is the strain when creep breaking occurs, is almost constant regardless of the temperature or stress. In order to create a reliable lifespan-assessment diagram, the creep test is carried out with the use of at least 3, preferably 8 or more, and more preferably 10 or more combinations of stresses and test temperatures. In each instance of the creep test, the following factors are determined: the elongation rate of a test material in relation to the creep breaking elongation obtained when the lifespan of the test material is regarded as having elapsed (life-elongation rate); and the time period until the lifespan of a test material is regarded as having elapsed (life-time). The lifespan point on the creep elongation curve of a test material can be arbitrarily determined depending on requirements requested for a bolt to be assessed.

In general, it is thought that metallic material lifespan lasts until or close to the occurrence of metal breaking. When metal breaking takes place due to creep, creep involves the following: primary creep (first-stage creep) during which the strain velocity decreases; secondary creep (second-stage creep) during which the strain velocity remains substantially unchanged; and the tertiary creep (third-stage creep) during which the strain velocity increases. However, bolts that are used for fastening of pipes or casings become unable to function as bolts after transition to the tertiary creep. Because, even if breaking does not take place, leakage or the like is induced due to a sharp increase in strain. Therefore, in the present invention, it is preferable to regard the time to onset of the tertiary creep as corresponding to the bolt life. Accordingly, in the present invention, it is preferable to determine the time to onset of the tertiary creep as the life-time and to determine the elongation rate at the time to onset of the tertiary creep as the life-elongation rate.

Figure 2:
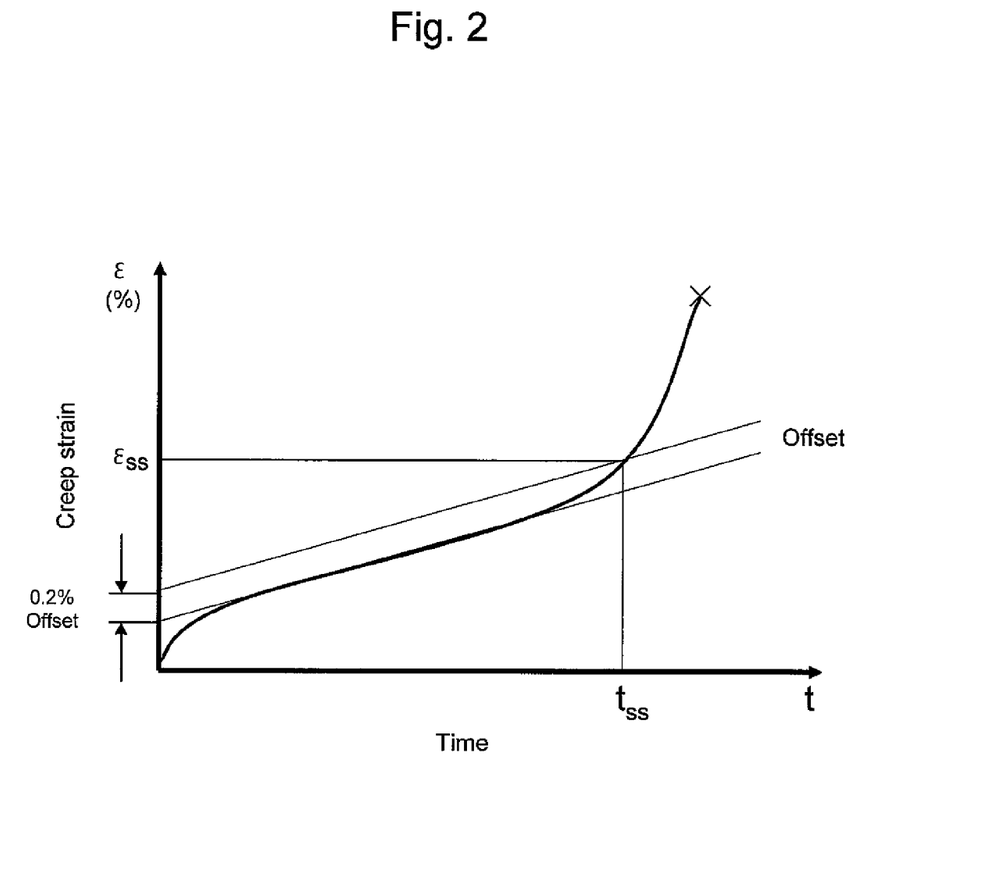
FIG. 2 schematically shows a method for obtaining the tertiary creep initiation time and the tertiary creep initiation strain based on the creep elongation curve.

The tertiary creep initiation point on the creep elongation curve can be determined by a method generally used by persons skilled in the art. For instance, as shown in FIG. 2, a crossing point of the creep elongation curve and the straight line obtained by offsetting an arbitrary strain rate (e.g., 0.02% to 0.2%) based on the gradient of the secondary creep (transition region) can be designated as the tertiary creep initiation point.

The term "time-temperature parameter" used in the present invention refers to a breaking parameter ($P_r$) that is generally used for assumption of long-term behavior based on short-term test results for assumption of creep breaking time. Examples of major time-temperature parameters include parameters of Orr-Sherby-Dorn (Equation A), Larson-Miller (Equation B), and Manson-Haferd (Equation C) parameters described below:

$$P_r = \log t_r - Q \log e/RT \quad \text{(Equation A)}$$

$$P_r = (\log t_r - \log t_0)T \quad \text{(Equation B)}$$

$$P_r = (\log t_r - \log t_0)/(T-T_0) \quad \text{(Equation C)}$$

[wherein "Q" represents activation energy, "$t_0$" and "$T_0$" each represent a parameter constant, "R" represents a gas constant, "T" represents creep test temperature, and "$t_r$" represents breaking time].

The time-temperature parameter can be appropriately selected depending on the bolt material or the like for a bolt to be assessed such that the parameter can be approximated to a predetermined function (preferably a straight-line function) when plotted with respect to the life-elongation rate. For instance, among the parameters of Equations A to C described above, the Manson-Haferd parameter can be appropriately used for the assessment method of the present invention. The Manson-Haferd parameter is particularly preferable for a bolt material composed of ferritic forged steel containing 8% to 13% by mass of Cr.

The lifespan assessment line in the lifespan-assessment diagram can be obtained by plotting the time-temperature parameter with respect to the life-elongation rate and obtaining the function for approximating plotted points (preferably a straight-line function). If the lifespan assessment line is experimentally obtained for each bolt material, the remaining bolt lifespan can be easily assessed by obtaining a time-temperature parameter based on the temperature of the atmosphere in which the bolt is used and the time of the use of the bolt, measuring the elongation rate for the bolt between before and after the use of the bolt, and plotting the obtained time-temperature parameter and the elongation rate on the lifespan-assessment diagram. In addition, based on the above lifespan-assessment diagram, a method for assessing remaining lifespan of bolt that can be applied to a wide stress range can be provided.

The remaining bolt lifespan can be obtained as, for example, the life consumption rate. For instance, the life consumption rate $\Phi$ can be obtained by the following "Equation a" based on the bolt elongation rate:

$$\Phi = \frac{[\text{life-elongation rate}] - [\text{bolt elongation rate}]}{[\text{life-elongation rate}]} \quad \text{(Equation a)}$$

The life-elongation rate can be obtained by determining the time-temperature parameter value based on conditions for the use of a bolt and assigning such value to the lifespan assessment line function.

In addition, it is also possible to carry out bolt lifespan assessment with the use of the lifespan-assessment diagram by a method comprising comparing the life-time and the bolt use time at a predetermined bolt elongation rate. In this case, the life consumption rate $\Phi$ can be obtained by the following "Equation b:"

$$\Phi = \frac{[\text{life-time}] - [\text{used time of bolt}]}{[\text{life-time}]} \quad \text{(Equation b)}$$

The life-time can be determined with the use of the time-temperature parameter value obtained by assigning the bolt elongation rate to the lifespan assessment line function, the temperature of the atmosphere in which a bolt is used, and the time-temperature parameter equation.

The bolt elongation rate that is used for remaining bolt lifespan assessment can be obtained by measuring bolt elongation based on comparison of a bolt to be assessed in an unused state and that in a used state. Such measurement can be carried out when, for example, regular inspection is carried out for a chemical plant or a turbine under shutdown conditions. According to the assessment method of the present invention, it is not particularly necessary to continuously measure bolt elongation during operation at high temperatures. Therefore, remaining bolt lifespan assessment can be readily carried out. Measurement of bolt elongation can be carried out by a general determination method involving, for example, contact determination with the use of a slide gauge or optical or electromagnetic non-contact determination. In order to carry out the method for assessing the remaining lifespan with higher precision, it is preferable to carry out measurement of bolt elongation in a more precise manner. In addition, if a bolt is assessed as having not experienced consumption as a result of remaining lifespan assessment, it can be used again.

A bolt material examined by the assessment method of the present invention is not particularly limited. However, a preferable bolt material used at high temperatures is a ferritic forged steel containing 8% to 13% by mass of Cr. A particularly preferable example of such material is a ferritic forged steel containing C (0.05% to 0.20% by mass and preferably 0.09% to 0.15% by mass), Si (0.2% by mass or less and preferably 0.15% by mass or less), Mn (0.01% to 1.5% by mass, preferably 0.1% to 0.7% by mass, and more preferably 0.35% to 0.65% by mass), Ni (0.005% to 0.60% by mass, preferably 0.01% to 0.50% by mass, and more preferably 0.1% to 0.4% by mass), Cr (8.0% 13.0% by mass and preferably 9.0% to 12.0% by mass), Mo (0.05% to 2.0% by mass and preferably 0.05% to 1.5% by mass), W (0.2% to 5.0% by mass and preferably 0.3% to 3.0% by mass), V (0.05% to 0.30% by mass and preferably 0.15% to 0.30% by mass), at least one of Nb and Ta (0.01% to 0.20% by mass and preferably 0.04% to 0.15% by mass), Co (3% by mass or less), N (0.01% to 0.1% by mass and preferably 0.01% or 0.04% by mass), B (0.0001% to 0.030% by mass and preferably 0.005% to 0.025% by mass), and Al (0.0005% to 0.04% by mass).

C is an essential element for securing quenching performance and allowing an $M_{23}C_6$-type carbide to precipitate during tempering so as to improve high-temperature strength. The minimum necessary content of C is 0.05% by mass. However, when the content of C exceeds 0.20% by mass, an $M_{23}C_6$-type carbide excessively precipitates, resulting in a decrease in the matrix strength and loss of long-term high-temperature strength. Therefore, the content is preferably 0.05% to 0.20% by mass and particularly preferably 0.09% to 0.15% by mass.

Si promotes generation of the Laves phase and reduces ductibility as a result of grain boundary segregation or the like. Therefore, the content of Si is preferably limited to 0.20% by mass or less and particularly 0.15% by mass or less. However, when Si is added as an deoxidizing agent to result in a minute content of 0.01% by mass or more, good high-temperature characteristics can be obtained in relation to Al deoxidation described below.

Mn is an element that suppresses generation of δ-ferrite and promotes precipitation of an $M_{23}C_6$-type carbide. The minimum necessary content of Mn is 0.01% by mass. However, when the content exceeds 1.5% by mass, oxidation resistance deteriorates. Therefore, the content is preferably 0.01% to 1.5% by mass, more preferably 0.1% to 0.7% by mass, and particularly preferably 0.35% to 0.65% by mass.

Ni is an element that suppresses generation of δ-ferrite and imparts toughness. The minimum necessary content of Ni is 0.005% by mass. However, when the content exceeds 0.6% by mass, high-temperature strength decreases. Therefore, the content is preferably 0.005% to 0.60% by mass, more preferably 0.01% to 0.50% by mass, and particularly preferably 0.1% to 0.50% by mass.

Cr is an essential element for imparting oxidation resistance and allowing an $M_{23}C_6$-type carbide to precipitate so as to improve high-temperature strength. The minimum necessary content of Cr is 8% by mass. When the content exceeds 13% by mass, δ-ferrite is generated, resulting in reduction in high-temperature strength and toughness. Therefore, the content is preferably 8.0% to 13.0% by mass and particularly preferably 9.0% to 12.0% by mass.

Mo has a function of promoting fine precipitation of an $M_{23}C_6$-type carbide, thereby preventing aggregation. Therefore, it is effective for maintaining high-temperature strength for many hours. The minimum necessary content of Mo is 0.05% by mass. However, when the content is 2.0% by mass or more, δ-ferrite tends to be generated. Accordingly, the content is preferably 0.05% to 2.0% by mass and particularly preferably 0.05% to 1.5% by mass.

W has a stronger effect of suppressing aggregation and coarsening of an $M_{23}C_6$-type carbide than Mo. In addition, W causes solution hardening of a matrix and therefore it is effective for promoting high-temperature strength. The minimum necessary content of W is 0.2% by mass. However, when the content exceeds 5.0% by mass, δ-ferrite and the Laves phase tend to be generated, which adversely results in reduction of high-temperature strength. Therefore, the content is preferably 0.3% to 3.0% by mass.

V is effective for allowing a carbonitride of V to precipitate so as to improve high-temperature strength. The minimum necessary content of V is 0.05% by mass. However, when the content exceeds 0.3% by mass, carbon is excessively immobilized and the amount of an $M_{23}C_6$-type carbide that precipitates decreases, which adversely results in reduction of high-temperature strength. Therefore, the content is preferably 0.05% to 0.3% by mass and particularly preferably 0.15% to 0.30% by mass.

At least one of Nb and Ta is useful for obtaining fine crystal particles by generating NbC or TaC. In addition, a portion thereof is present in a solid solution form upon quenching so as to cause NbC or TaC to precipitate during tempering, thereby improving high-temperature strength. The minimum necessary content of Nb or Ta is 0.01% by mass. However, when the content exceeds 0.20% by mass, carbon is excessively immobilized as in the case of V, and thus the amount of an $M_{23}C_6$-type carbide that precipitates decreases, resulting in reduction of high-temperature strength. Therefore, the content is preferably 0.01% to 0.20% by mass and particularly preferably 0.04% to 0.15% by mass.

Co has an effect of suppressing generation of δ-ferrite and also an effect of improving high-temperature strength as a result of solution hardening. However, Co is an expensive element. Therefore, the upper limit of the content thereof is preferably approximately 3% by mass. When it is used at 600° C. or more, the effective content is 1.0% by mass or more.

N has an effect of allowing a nitride comprising V to precipitate and an effect of improving high-temperature strength when present in a solid solution form as a result of IS effects (interaction between an invasive solid solution element and a substitutional solid solution element) in cooperation with Mo or W. The minimum necessary content of N is 0.01% by mass. However, when the content exceeds 0.1% by mass, ductibility is reduced. Therefore, the content is preferably 0.01% to 0.1% by mass and particularly preferably 0.01% to 0.04% by mass.

B has an effect of enhancing grain boundary formation. It also functions to suppress aggregation and coarsening of an $M_{23}C_6$-type carbide when present in a solid solution form in $M_{23}C_6$ so as to exhibit an effect of improving high-temperature strength. It is effective to add B, provided that the minimum necessary content thereof is 0.0001% by mass. However, when the content exceeds 0.030% by mass, toughness is reduced, resulting in inhibition of forgeability. Therefore, the content is preferably 0.0001% to 0.030% by mass and particularly preferably 0.0005% to 0.025% by mass.

It is preferable to add Al as a deoxidizing agent and as an agent for forming fine crystal particles to result in an Al content of 0.0005% by mass or more. However, since Al is an element that constitutes a strong nitride, it adheres to nitrogen that effectively acts to prevent creep. Therefore, it has an effect of causing a decrease in the long-term creep strength when the content thereof exceeds 0.040% by mass. Accordingly, it is preferable to set the upper limit of such content at 0.040% by mass. Particularly preferably, the content of Al added is 0.001% to 0.030% by mass.

EXAMPLES

The present invention is hereafter described in greater detail with reference to the following examples, although the technical scope of the present invention is not limited thereto.

1. Creation of a Lifespan-Assessment Diagram

First, a bolt material was subjected to a creep test. A lifespan-assessment diagram was created, with the time to tertiary creep designated as the bolt life. Table 1 shown below lists the chemical composition of the bolt material used.

TABLE 1

| C | Si | Mn | P | S | Ni | Cr | W | Mo | V | Nb | Co | Al | N | B |
|---|---|---|---|---|---|---|---|---|---|---|---|---|---|---|
| 0.1 | 0.04 | 0.5 | 0.005 | 0.004 | 0.5 | 10.5 | 2.5 | 0.2 | 0.2 | 0.1 | 2.5 | 0.01 | 0.02 | 0.01 |

Unit: % by mass

Starting materials were melted by the electroslag remelting method and a sample was prepared by hot forging. The sample was subjected to quenching (1100° C.×1 hour, oil cooling), followed by tempering (700° C.×4 hours, air cooling). A plurality of creep test pieces were taken from the sample. A creep test was conducted at different stresses in an atmosphere at 570° C., 600° C., 625° C., or 650° C. A plurality of creep elongation curves were obtained at different temperatures and stresses.

FIG. 2 schematically shows how to obtain the tertiary creep initiation time and the tertiary creep initiation strain (strain at the time to onset of the tertiary creep initiation (elongation rate)) based on creep elongation curves. As shown in FIG. 2, the tertiary creep initiation time ($t_{ss}$) and the tertiary creep initiation strain ($\epsilon_{ss}$) were obtained by defining the tertiary creep initiation point and the crossing point of a creep elongation curve and a straight line obtained by 0.2% offset of the strain rate based on the gradient of the secondary creep (transition region).

Figure 3:
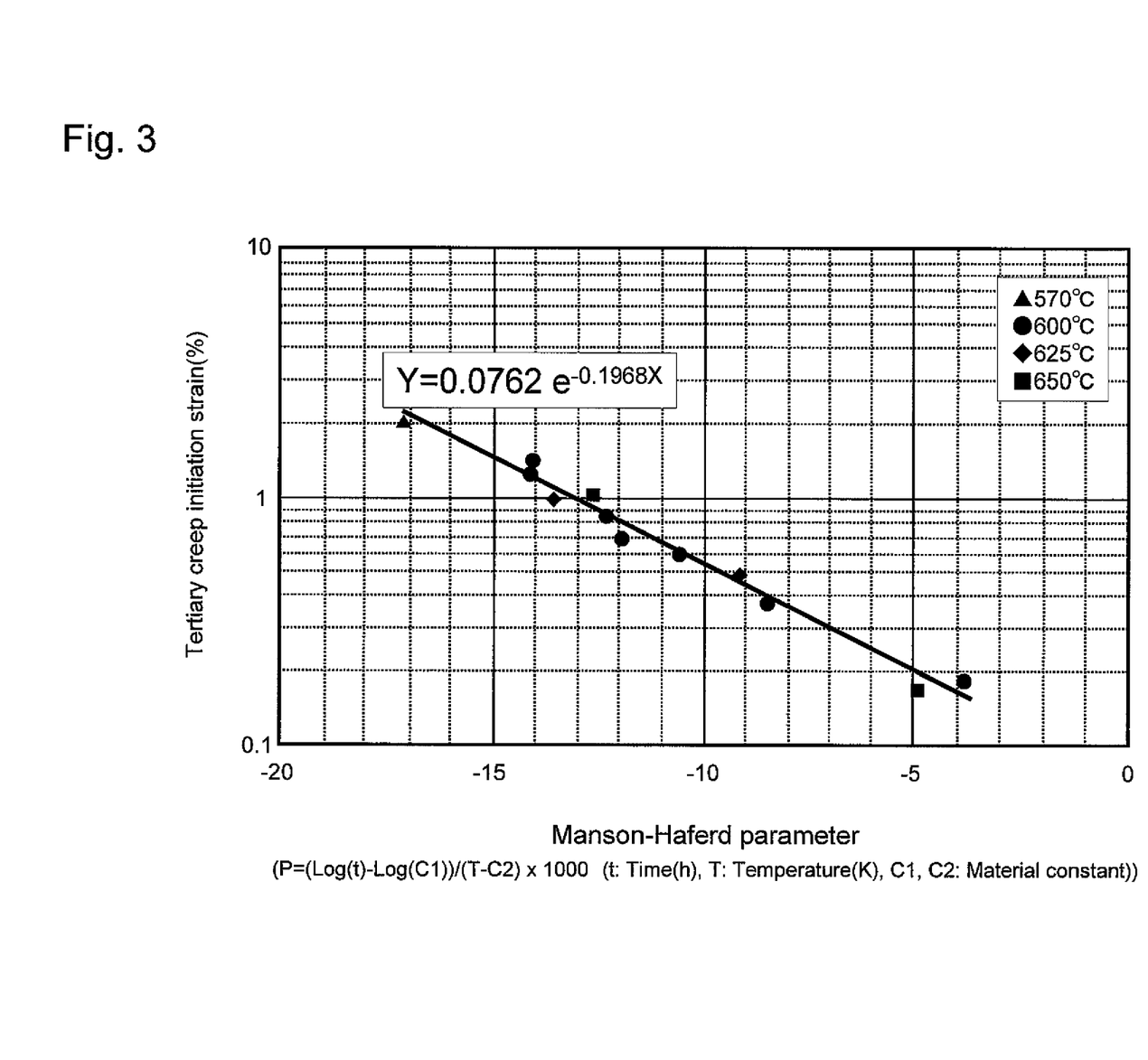
FIG. 3 shows a lifespan-assessment diagram obtained from the example.

Next, with the use of the creep test temperature and the obtained the tertiary creep initiation time ($t_{ss}$), Manson-Haferd parameter was obtained. Then, a lifespan-assessment diagram was created by plotting the tertiary creep initiation strain with respect to the Manson-Haferd parameter. FIG. 3 is the lifespan-assessment diagram. It has been revealed that when "Y" represents tertiary creep initiation strain and "X" represents a Manson-Haferd parameter, the relationship therebetween can be approximated by the following Equation I.

$$Y = 0.0762 e^{-0.1968X}$$ (Equation I)

2. Evaluation of Bolts with the Use of the Lifespan-Assessment Diagram

First, a bolt fastening test was conducted as described below in order to obtain bolts in a state of having experienced consumption and bolts in a state of retaining life. Bolts were prepared such that each had an entire length ($L_0$) of 300 mm and a shank portion length ($l_o$) of 240 mm Bolts were fastened at two different initial fastening stresses and subjected to a bolt fastening test in a test environment that simulated fastening of a steam turbine casing (temperature: 580° C.). After the elapse of approximately 50,000 hours, steam leakage was confirmed for one of the bolts, and therefore such bolts were regarded as having experienced lifespan consumption. Then, the test was terminated. Hereinafter, a bolt that experienced steam leakage is referred to as "bolt A" and a bolt that did not experience steam leakage is referred to as "bolt B."

Figure 4:
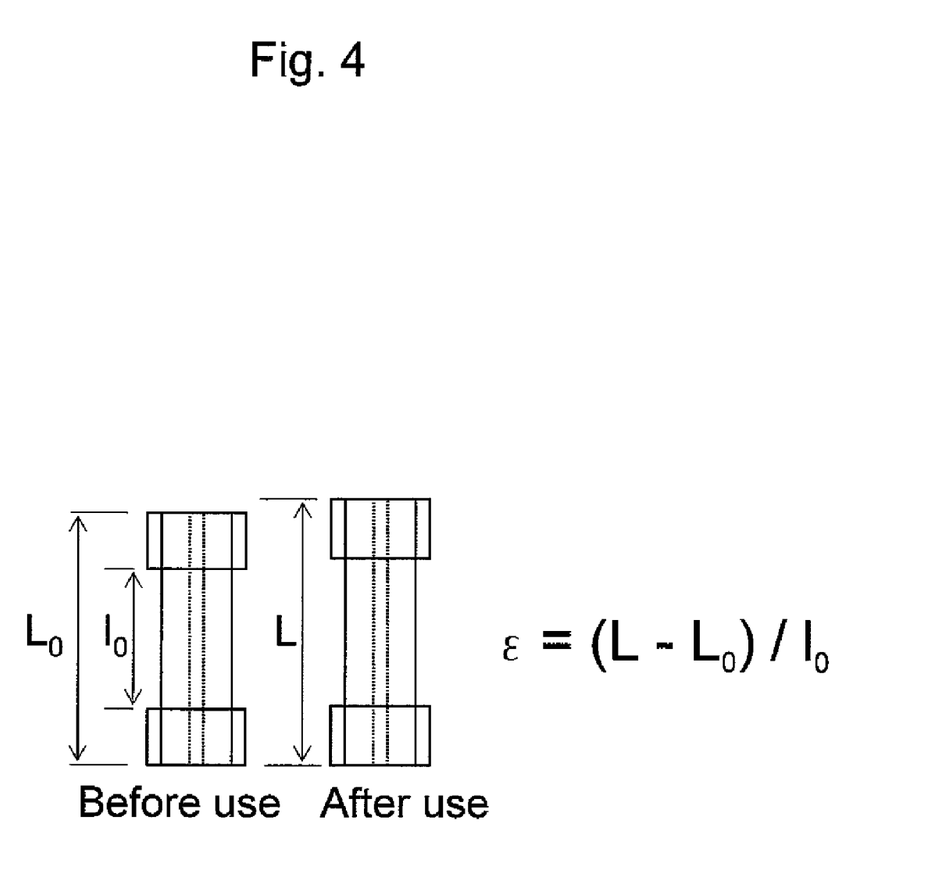
FIG. 4 shows a method for determining bolt strain rate.

Next, bolt elongation was measured and then the remaining lifespan of each bolt was assessed based on the lifespan-assessment diagram. FIG. 4 explains the method for measuring bolt strain rate. In a bolt, creep deformation is observed only in the shank portion. Therefore, the bolt strain rate ($\epsilon$) can be obtained by the following Equation II with the entire bolt length ($L_0$) obtained before use, the shank portion length ($l_0$) obtained before use, and the entire bolt length (L) obtained after use.

$$\epsilon = (L-L_0)/(l_0) \quad \text{(Equation II)}$$

In the case of a bolt A, the entire length was elongated by 1.2 mm after use and the strain rate was 0.50%. In the case of a bolt B, the entire length was elongated by 0.65 mm after use and the strain rate was 0.27%.

Figure 5:
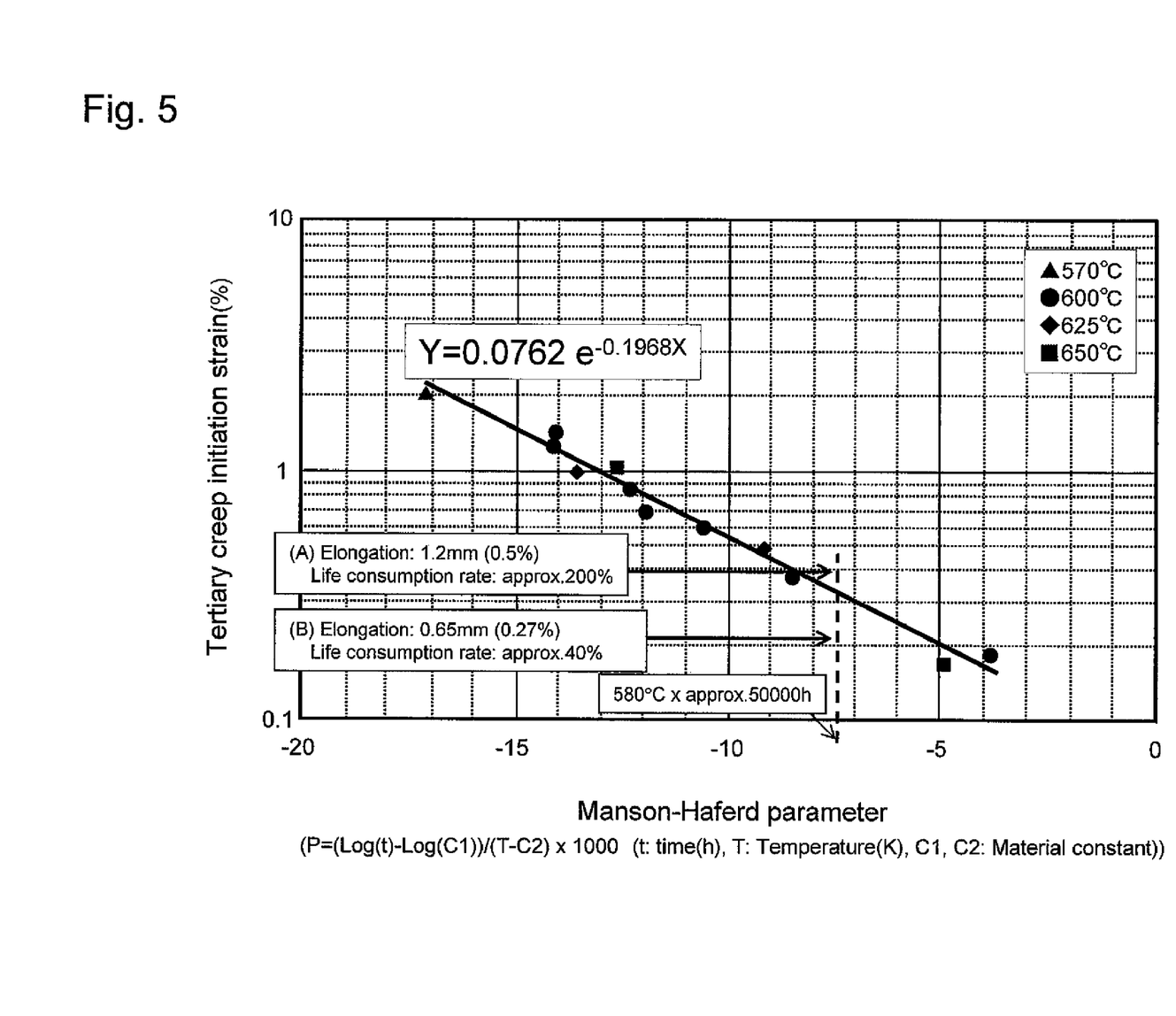
FIG. 5 shows a method for assessing the remaining lifespan of a bolt with the use of the lifespan-assessment diagram.

FIG. 5 explains the method for assessing the remaining lifespan of bolts A and B with the use of the lifespan-assessment diagram. First, a Manson-Haferd parameter was obtained at a test temperature of 580° C. for a test time of approximately 50,000 hours. As a result, the value shown in FIG. 5 was obtained. Based on the value and the function represented by Equation I, the remaining lifespan for each bolt was assessed based on the bolt strain rate. In addition, based on the tertiary creep initiation strain ($\epsilon_{ss}$) and the bolt strain rate ($\epsilon$), the consumption rate ($\Phi$) was obtained by the following Equation III.

$$\Phi = (\epsilon_{ss}-\epsilon)/\epsilon_{ss} \quad \text{(Equation III)}$$

In the cases of bolts A that had experienced steam leakage, the obtained values were plotted above the function represented by Equation I and the consumption was approximately 200%. Therefore, it was assessed that consumption of bolts A had taken place. In the cases of bolts B that did not experience steam leakage, the obtained values were plotted below the function represented by Equation I and the consumption was approximately 40%. Therefore, it was assessed that bolts B retained life.

All references, including any publications, patents or patent applications cited in this specification are hereby incorporated by reference in their entirely.

What is claimed is:

1. A method for assessing remaining lifespan of a bolt used at high temperatures, comprising:
    carrying out a creep test for a bolt material that constitutes a bolt to be assessed and determining a life-time and a life-elongation rate;
    determining a time-temperature parameter based on the life-time and the creep test temperature;
    creating a lifespan-assessment diagram by plotting the time-temperature parameter with respect to the life-elongation rate;
    measuring a elongation rate between before and after the use of the bolt to be assessed; and
    assessing the remaining lifespan of the bolt with the use of the elongation rate between before and after the use of the bolt to be assessed and the lifespan-assessment diagram.

2. The method for assessing remaining lifespan of a bolt according to claim 1, wherein the life-time corresponds to the time to onset of the tertiary creep and the life-elongation rate corresponds to the elongation rate at the time to onset of the tertiary creep.

3. The method for assessing remaining lifespan of a bolt according to claim 1, wherein the bolt used at high temperatures is for a turbine pipe, a turbine valve, or a turbine casing.

4. The method for assessing remaining lifespan of a bolt according to claim 1, wherein the bolt material is a ferritic forged steel containing 8% to 13% by mass of Cr.

5. The method for assessing remaining lifespan of a bolt according to claim 1, wherein the time-temperature parameter is Manson-Haferd parameter.

* * * * *